United States Patent [19]

Bönnemann et al.

[11] Patent Number: 4,469,638
[45] Date of Patent: Sep. 4, 1984

[54] PRODUCTION OF TRANSITION METAL COMPLEXES

[75] Inventors: Helmut Bönnemann, Essen-Ruhr; Borislav Bogdanovic, Mülheim, both of Fed. Rep. of Germany

[73] Assignee: Studiengesellschaft Kohle mbH, Mulheim, Fed. Rep. of Germany

[21] Appl. No.: 466,813

[22] Filed: Feb. 16, 1983

[30] Foreign Application Priority Data

Feb. 17, 1982 [DE] Fed. Rep. of Germany ....... 3205550

[51] Int. Cl.$^3$ ............ C07F 15/06; C07F 15/04; C07F 17/00; C07F 17/04; C07F 7/28; C07F 7/22
[52] U.S. Cl. ............ 260/439 CY; 260/429 CY; 260/429 R; 260/429.3; 260/439 R; 260/441; 260/446
[58] Field of Search ............ 260/439 CY, 429 CY

[56] References Cited

U.S. PATENT DOCUMENTS

| 3,959,220 | 5/1976 | Hechenbleikner et al. ... 260/439 CY X |
| 4,006,149 | 2/1977 | Bonnemann et al. ............... 546/250 |
| 4,012,399 | 3/1977 | Hechenbleikner et al. ... 260/439 CY X |
| 4,017,526 | 4/1977 | Wilke et al. .................. 260/439 CY |
| 4,104,036 | 8/1978 | Chao et al. ............................... 44/56 |
| 4,266,061 | 5/1981 | Bönnemann et al. ............... 546/350 |
| 4,267,329 | 5/1981 | Bönnemann et al. .... 260/439 CY X |

*Primary Examiner*—Helen M. S. Sneed
*Attorney, Agent, or Firm*—Sprung, Horn, Kramer & Woods

[57] ABSTRACT

The invention relates to a process for the production of complex compounds of the transition metals which is characterized in that transition metals are reacted with magnesium, to which a catalytic quantity of anthracene and/or magnesium anthracene has been added as activator, in the presence of complexing ligands.

6 Claims, No Drawings

PRODUCTION OF TRANSITION METAL COMPLEXES

This invention relates to a general process for the synthesis of transition metal complexes by reacting transition metal compounds with specially activated magnesium in the presence of complexing electron donors. Several processes for the production of transition metal complexes using reducing alkali and alkaline-earth metals have been described, magnesium being particularly advantageous in terms of economy, non-toxic, safe handling and availability.

Thus the reaction of nickel salts with particulate magnesium in the presence of triphenyl phosphane is described in as early a publication as DAS No. 11 26 864. However, the nickel complex formed through this reaction cannot be isolated, but instead is used in situ as a catalyst. DOS No. 14 43 461 describes the production of a nickel catalyst by reacting nickel compounds with inter alia magnesium metal in the presence of 1,3-dienes. No nickel-olefin complex is formed in this case either. The in situ reaction of nickel compounds with magnesium in the presence of phosphanes is also described in DOS No. 22 21 113, although no complex compound of nickel is characterized as such. These processes are clearly unsuitable for the production of transition metal complex compounds of defined composition. Italian Pat. No. 887,228 (C.A. 83, 28373) describes the production of bis(cyclo-(1,5)-octadiene) nickel from nickel halides and cyclo-(1,5)-octadiene by reaction inter alia with magnesium. However, the product is decomposable and requires the addition of stabilizers.

However, pure storable substances are required for commercial applications. Klein and Karsch reported on the synthesis of tetrakis(trimethylphosphane)-cobalt (O) with magnesium metal as reducing agent in a reaction lasting 24 hours (H.-F. Klein and H. H. Karsch, Chem. Ber. 108, 944–955 (1975)). Finally, G. Wilke and W. Gausing used magnesium metal for the reductive synthesis of tris(butadiene)-molybdenum and -tungsten (Angew. Chem. 93, 201–202 (1981)). In this case, the reaction time was 48 hours. However, faster production processes are required for commercial applications. In addition, the reactivity of magnesium metal depends to a large extent upon the size and purity of its active surface (cf. for example J. R. Blackborrow, D. Young: "Metal Vapour Synthesis in Organometallic Chemistry", Springer-Verlag 1979 page 179). Hitherto, there has never been a satisfactory process for the economic production of transition metal complexes using magnesium as reducing agent.

There has been no shortage of attempts to improve the reactivity of magnesium metal by the addition of activators and accelerators (cf. for example Y.-H. Lai, Synthesis 1981, 586). Accelerators and activation techniques such as these have also been occasionally used for the heterogeneous reaction of transition metal salts with magnesium. Thus, DOS No. 23 53 198 and DOS No. 23 53 240 describe a process for the production of a zerovalent nickel complex using inter alia magnesium and zinc halides or ammonium halides as accelerators in organic nitriles as solvents. For technical purposes, however, nitriles are generally uneconomical as solvents and the addition of foreign metal salts, such as zinc halides, complicates purification of the products.

For the reduction of certain cyclopentadienyl transition metal halides with magnesium, M. D. Rausch and D. J. Sikora (J. Am. Chem. Soc. 103, 1265–1267 (1981)) use mercury chloride as activator or employ a magnesium obtained from magnesium chloride using potassium metal (cf. R. E. Rieke et. al., J. Am. Chem. Soc. 96, 1775–1781 (1974)). These activation processes are highly involved when applied on a commercial scale and require the use of highly toxic mercury.

It has now surprisingly been found that the addition of a catalytic quantity of anthracene and/or or magnesium anthracene to magnesium produces a highly active reducing agent which is as inexpensive as it is easy to handle and which generally enables transition metal compounds to be economically reacted in the presence of complexing ligands to form complex compounds of the transition metals.

To produce the complex compounds by the process according to the invention, from 1 to 10 mole percent and preferably from 2 to 6 mole percent of anthracene is initially added to magnesium metal powder, which preferably has a particle size of less than 0.15 mm, in a solvent, preferably tetrahydrofuran or diglyms. Although the addition of an alkyl halide, such as methyl iodide, is favorable, it is not crucial to the process according to the invention. After 1 to 3 hours, a highly active magnesium is obtained in addition to a small quantity of magnesium anthracene and may be used for reduction of the transition metal salts in the presence of complexing ligands under mild conditions. In one variant of the process according to the invention, preformed magnesium anthracene is added as activator. Carrying out activation in an ultrasonic bath promotes the formation of a clean metal surface. According to the invention, the transition metal salts and the complexing ligands are contacted with the magnesium/anthracene system or magnesium anthracene at temperatures in the range from $-78°$ C. to $+150°$ C. and preferably at temperatures in the range from $-30°$ C. to $+80°$ C., the reaction being accompanied by the evolution of heat and being complete within a few minutes to at most 3 hours.

In this connection, it is important that anthracene or magnesium anthracene act as catalysts for the production of highly reactive Mg-species during reaction of the magnesium with the particular transition metal salts. The omission of these activation catalysts results in considerably poorer complex yields or in incomplete reduction of the starting product, as shown by comparison tests (cf. for example Examples 7, 8 and 29). As is typical of a catalyst, the readily separable anthracene may be recovered from the reaction mixtures and re-used (Example 22).

Preferred transition metals are the elements of Groups IVB to VIIIB of the Periodic System of Elements, whilst preferred transition metal salts or compounds are those which contain either inorganic or organic anions, preferably those which are solvated in the systems used as solvent, such as halides, alcoholates and salts of organic acids. Examples of transition metals of Groups IVB, VB, VIB, VIIB and VIIIB of the Periodic System are titanium, zirconium, hafnium, vanadium, niobium, tantalum; chromium, molybdenum, tungsten; mangangese, technetium, rhenium; iron, cobalt, nickel, ruthenium, rhodium, palladium, osmium, iridium, platinum.

Suitable complexing agents are in general electron donors which form penetration complexes with transition metals. Electron donors such as these are compounds containing C—C-multiple bonds, such as olefins, for example ethylene, and also substituted olefins, such as methylene cyclopropane, stilbene, maleic acid anhydride or acrylonitrile, cyclic olefins, such as cyclopropene derivatives, norbornene, cyclic poly olefins, such as cyclooctadiene, cyclopentadiene and derivatives thereof, cyclododecatriene, and also polyolefins, such as allene, and conjugated olefin systems, such as 1,3-dienes (for example butadiene, isoprene, methylheptatriene), sorbic acid esters, also alkines, such as acetylene, 2-butine, tolane, and cycloalkines, such as for example cyclododecine. Other suitable electron donors are ligands containing free electron pairs, such as phosphanes, phosphites, arsanes, triorganyl antimony compounds, pyridines and dipyridines, carbon monoxide and also combinations of various complexing agents.

The process according to the invention enables magnesium, which is inexpensive, non-toxic and safe to handle, to be generally and effectively used for the first time for the production of transition metal complexes. In this connection, the following classes of complex compounds of the transition metals may be obtained with particular advantage using magnesium as reducing agent: $\eta^5$-cyclopentadienyl-transition metal complexes (metallocenes); $\eta^5$-cyclopentadienyl-cobalt-olefin half-sandwich compounds which cannot be obtained in a single stage by known methods; $\eta^3$-allyl-complexes of the transition metals, preferably nickel and cobalt, in the presence of 1,3-dienes; olefin complexes, particularly bis-(cyclooctadiene)-complexes and butadiene complexes of zerovalent transition metals, such as Ni, Pd, Pt and Mo; MTL$_n$-complexes of the transition metals, MT representing a zerovalent transition metal, L a neutral ligand, such as phosphane or phosphite, and n being a number of from 2 to 5; metallocene dihalides, particularly $\eta^5$-cyclopentadienyl titanium dihalides.

The complex compounds which may be inexpensively obtained in accordance with the present invention are used for example as catalysts in industrial chemistry (P. W. Jolly in: Ullmann's Enzyklopadie der Technischen Chemie, Vol. 16, pages 587 et seq.). Ferrocene is used as an addition in the low-smoke combustion of mineral oils.

Cobaltocenes and cyclopentadienyl-cobalt half-sandwich complexes are used as catalysts in the production of pyridine derivatives from alkines and nitriles [cf. H. Bonnemann, Angew. Chemie 90, 517 (1978) and also U.S. Pat. No. 4,006,149 and DBP No. 2,840,460] and also in the production of pyridine derivatives (cf. Examples 16, 17, 18, 19, 20 and 21 of the present application).

Bicycloocta-(1,5)-diene nickel is widely used in the synthesis of nickel complexes by ligand exchange [Inorg. Synth. XV, 5 (1974)] and as a catalyst in organic synthesis, especially in the production of natural substances [P. W. Jolly and G. Wilke; The Organic Chemistry of Nickel, Vol. II, Academic Press (1975), and also P. W. Jolly and G. Wilke in Merck Kontakte, 21, (1974)]. Tetrakis-triphenyl phosphane palladium is used as a catalyst in the functionalization of olefins [J. Tsuji in: Adv. in organomet. Chem. 17 (1979), pages 141 et seq.]. Phosphite complexes of nonvalent nickel enable butadiene to be catalytically hydrocyanated to form adipic acid nitrile on an industrial scale [Chem. Eng. News, Apr. 26, 1971, 30; Chem. Week, May 12, 1971, 32–37]. In addition, metallocene dihalides, for example of titanium, are of interest as potential cytostatic agents (cf. H. Kopf and P. Kopf-Maier, Nachr. Chem. Techn. Lab. 29 (1981), page 154).

EXAMPLE 1

Cobaltocene 1.1 g (6.2 mMoles) of anthracene, 300 ml of THF and 0.1 ml of methyliodide are added to 14.4 g (600 mMoles) of magnesium powder (particle size <0.15 mm) in an inert gas atmosphere. A yellow-green solution is formed with stirring at 20° C., orange-colored magnesium anthracene precipitating therefrom after about 2 hours. The reaction mixture is treated for about 3 hours in an ultrasonic bath (continuous peak HF output 240 watts, 35 kHz) and then heated with stirring to 60° C. After the addition of 19.8 g (300 mMoles) of monomeric cyclopentadiene, the heat source is removed and 35.6 g (100 mMoles) of solid cobalt-(III) acetyl acetonate are added over a period of 20 minutes. The reaction mixture changes color to dark brown with vigorous evolution of heat and begins refluxing (66° C.). After cooling to 20° C., the reaction mixture is filtered off from unreacted magnesium through a G-3-glass frit and the clear dark brown filtrate is concentrated by evaporation to dryness (max. bath temperature 30° C.) in a high vacuum ($10^{-3}$ Torr). The residue is taken up in 500 ml of pentane and any undissolved fractions are isolated by filtration through a G-3-glass frit. The filter cake is washed several times with a total of 500 ml of pentane until the filtrate is substantially colorless. The clear red-brown filtrate is concentrated to approximately 200 ml and the complex is left to crystallize out at −80° C. The supernatant mother liquor is removed under pressure and washed 2 to 3 times with approximately 50 ml of pentane cooled to −80° C. Drying in vacuo (0.1 Torr) gives 12.4 g (63.7 mMoles = 63.7% of the theoretical) of pure cobaltocene in the form of black-violet crystals melting at 172.5° C., as measured in an inert gas atmosphere.

EXAMPLE 2

Bis-(indenyl)-cobalt 1.1 g (6.2 mMoles) of anthracene, 350 ml of THF and 0.1 ml of methyliodide are added to 14.4 g (600 mMoles) of magnesium powder (particle size <0.15 mm) in an inert gas atmosphere. A yellow-brown solution is formed while stirring at 23° C., orange-colored magnesium anthracene precipitating therefrom after 100 minutes. The reaction mixture is treated for about 3 hours in an ultrasonic bath (continuous peak HF output 240 watts, 35 kHz) and subsequently heated with stirring to 60° C. After the addition of 34.8 g (300 mMoles) of indene, the heat source is removed and 35.6 g (100 mMoles) of solid cobalt-(III) acetylacetonate are added over a period of 40 minutes. The reaction mixture changes color to dark brown with an increase in temperature to 68° C. After cooling to 23° C., the reaction mixture is filtered off from excess magnesium through a G-3-glass frit and the clear brown red filtrate is concentrated by evaporation to dryness (max. bath temperature 30° C.) in a high vacuum ($10^{-3}$ Torr). The residue is taken up in 500 ml of pentane and any insoluble fractions are isolated by filtration through a G-3-glass frit. The filter cake is washed several times with a total of 500 ml of pentane until the filtrate is substantially colorless. The clear red-brown filtrate is concentrated to approximately 200 ml and the complex left to crystallize out at −80° C. The supernatant mother liquor is removed under pressure and washed 2 to 3 times with approximately 50 ml of pentane cooled to −80° C.

Drying in vacuo (0.1 Torr) gives 10.3 g (35 mMoles = 35.5% of the theoretical) of bis-(indenyl)-cobalt in the form of glittering black crystals.

EXAMPLE 3

$\eta^5$-indenyl-$\eta^5$-cyclopentadienyl cobalt 1.1 g (6.2 mMoles) of anthracene, 300 ml of THF and 0.1 ml of methyliodide are added to 7.2 g (300 mMoles) of magnesium powder (particle size <0.15 mm) in an inert gas atmosphere. A yellow-brown solution is formed while stirring at 20° C., orange-colored magnesium anthracene precipitating therefrom after about 2 hours. The reaction mixture is treated for about 3 hours in an ultrasonic bath (as in Example 1) and then heated with stirring to 60° C. After the addition of 34.3 g (295.7 mMoles) of indene and 7.7 g (116.7 mMoles) of monomeric cyclopentadiene, the heat source is removed and 35.6 g (100 mMols) of solid cobalt-(III) acetylacetonate are added over a period of 20 minutes. The reaction mixture changes color to dark red-brown with a vigorous heat effect (temperature up to 70° C.). After cooling to 23° C., the reaction mixture is filtered off from any insoluble fractions and from unreacted magnesium through a G-3-glass frit and the clear red-brown filtrate is concentrated in vacuo ($10^{-2}$ Torr) until the sublimation of a red compound is observed. The vacuum is removed, the highly viscous, almost black residue is taken up in approximately 400 ml of pentane and any insoluble fractions are isolated by filtration through a G-3-frit. The filtrate is concentrated to dryness in a vacuum ($10^{-1}$ Torr) and a scarlet-red compound is sublimated from the violet-brown residue in a high vacuum ($10^{-3}$ Torr) at a bath temperature of 30° to 150° C. The sublimate is dissolved in approximately 100 ml of pentane, the resulting solution freed from any insoluble fractions through a G-3-frit and the clear, deep red filtrate is cooled to −80° C. The supernatant mother liquor is removed under pressure from the complex formed and the crystals are washed twice with 25 ml of pentane cooled to −80° C. Drying in vacuo ($10^{-1}$ Torr) gives 4.2 g of $\eta^5$-indenyl-$\eta^5$-cyclopentadienyl cobalt (17.6 mMoles = 17.6% of the theoretical) of scarlet-red needles melting at 173° C.

Mass spectrum: m/e: 239 (M+); 174, 124; 59.

EXAMPLE 4

Ferrocene

Following the procedure of Example 1, 0.6 g (3.4 mMoles) of anthracene are added to 3.6 g of magnesium powder in 300 ml of THF and the orange-colored reaction mixture is heated to 65° C. After the addition of 19.8 g (300 mMoles) of monomeric cyclopentadiene, 16.2 g (100 mMoles) of $FeCl_3$ are introduced over a period of 1 hour, the reaction mixture changing color to yellow-brown with vigorous evolution of heat. After cooling to 23° C., the reaction mixture is concentrated to dryness in vacuo and the residue is extracted with a total of 500 ml of pentane. The dark yellow extract is cooled to −80° C. and ferrocene is crystallized out. Drying in vacuo gives 12.9 g (69% of the theroetical) of ferrocene.

EXAMPLE 5

$\eta^5$-cyclopentadienyl cobalt cyclopentadiene 1.1 g (6.2 mMoles) of anthracene, 300 ml of THF and 0.1 ml of methyliodide are added with stirring in an inert gas atmosphere at 20° C. to 7.2 g (300 mMoles) of magnesium powder (particle size <0.15 mm). After about 2 hours, the reaction mixture is activated for about 3 hours in an ultrasonic bath (cf. Example 1). The mixture is then heated with stirring to 60° C. After the addition of 52.8 g (800 mMoles) of monomeric cyclopentadiene, the heat source is removed and 35.6 g (100 mMoles) of solid cobalt-(III)-acetylacetonate are added over a period of 30 minutes, the reaction mixture changing color to deep red-brown with a vigorous heat effect (65° C.). After cooling to 23° C., the reaction mixture is filtered off from any insoluble fractions through a G-3-glass frit and the deep red-brown filtrate is concentrated to dryness (max. bath temperature 30° C.) in vacuo ($10^{-1}$ Torr). The residue is taken up in 500 ml of pentane and any insoluble fractions eliminated by filtration. The clear deep red filtrate is concentrated to dryness (max. bath temperature 30° C.) in vacuo ($10^{-1}$ Torr) and the residue sublimated at $10^{-3}$ Torr (bath temperature up to 60° C., sublimation beginning at a bath temperature of 30° C.). The sublimate is dissolved in approximately 100 ml of pentane and the complex crystallized out at −80° C. 11.9 g (62.6 mMoles = 62.6% of the theoretical) of $\eta^5$-cyclopentadienyl cobalt cyclopentadiene are obtained in the form of wine-red crystals melting at 98° to 99° C.

Mass spectrum: m/e: 190 (M+).

EXAMPLE 6

$\eta^5$-methylcyclopentadienyl cobalt methylcyclopentadiene 1.1 g (6.2 mMoles) of anthracene, 300 ml of THF and 0.1 ml of methyliodide are added in an inert gas atmosphere to 7.2 g (300 mMoles) of magnesium powder (particle size <0.15 mm). A yellow-green solution is formed while stirring at room temperature, orange colored magnesium anthracene precipitating therefrom after about 2 hours. The reaction mixture is treated for about 3 hours in an ultrasonic bath (as in Example 1) and then heated while stirring to 60° C. After the addition of 32.0 g (400 mMoles) of monomeric methyl cyclopentadiene, the heat source is removed and 35.6 g (100 mMoles) of solid cobalt-(III)-acetylacetonate are added over a period of 30 minutes, the reaction mixture changing color to deep red-brown with a reflux-producing heat effect (65° C.). After cooling to 23° C., the reaction mixture is filtered off from any undissolved fractions through a G-3-glass frit and the deep red-brown filtrate is concentrated to dryness (max. bath temperature 30° C.) in vacuo ($10^{-1}$ Torr). The residue is taken up in 500 ml of pentane and any undissolved fractions are eliminated by filtration. The clear, deep red filtrate is concentrated to dryness (max. bath temperature 30° C.) in vacuo ($10^{-1}$ Torr) and the residue distilled at $10^{-3}$ Torr (bath temperature 80°–140° C.). 13.6 g (62.4 mMoles = 62.4% of the theoretical) of $\eta^5$-methylcyclopentadienyl cobalt methylcyclopentadiene are obtained in the form of a dark red oil which solidifies at around −5° C.

EXAMPLES 7 TO 21

The use of anthracene-activated magnesium for the production of cyclopentadienyl cobalt diolefin half-sandwich derivatives is illustrated in the form of a Table in Examples 9 to 21.

The procedure adopted is the same as in Example 1, anthracene initially being added to the magnesium, followed by ultrasonic treatment. The olefinic complex partners are then added together and the cobalt salts introduced into the mixture. Working up is carried out by changing the solvent from THF or diglyms to pentane.

The following abbreviations are used in the Table. Examples 7 and 8 are comparison examples *without* anthracene.

| | | |
|---|---|---|
| ac | = | acetate |
| acac | = | acetylacetonate |
| OEt | = | ethylate |
| Cp | = | $\eta^5$-cyclopentadienyl |
| CpH | = | cyclopentadiene |
| Ind | = | $\eta^5$-indenyl |
| Me | = | methyl |
| t-but | = | tert-butyl |
| COD | = | cycloocta-(1,5)-diene |
| NBD | = | norbornadiene |

The complexes denoted by an asterisk are hitherto unknown products and are described after the Table.

146.2 g of crude product are discharged from the autoclave and the volatile constituents removed by condensation at $10^{-3}$ Torr, 0.4 g of residue remaining behind. According to analysis by gas chromatography, the condensate (145.8 g) contains 80.88 g (1.973 moles) of acetonitrile, 52.58 g (0.565 mole) of 2-picoline and 8.61 g (0.110 mole) of benzene, corresponding to a 39.4% 2-picoline solution in acetonitrile. The molar ratio of 2-picoline to benzene is 5.1:1 and the yield of 2-picoline, based on the acetonitrile reacted, amounts to 69.5%. Conversion: 29.2% of acetonitrile. Catalyst utilization: 3749 moles of 2-picoline/g-atom of cobalt or 5913.6 kg of 2-picoline/kg of cobalt.

The use of trimethylsilyl cyclopentadienyl cobalt cycloocta-(1,5)-diene in the reaction of 2-cyanopyridine to form 2,2'-bipyridyl:

0.0360 g (0.1190 mMoles) of trimethylsilyl cyclopentadienyl cobalt cycloocta-(1,5)-diene and 52.4 g (0.5038 mole) of 2-cyanopyridine are dissolved in 100 ml (87.9

TABLE 1

| No. | Complex | Co-compound mMoles, addition time | Reducing agent/ activator mMoles/mMoles | Cyclopentadienyl compound mMoles | Olefin mMoles | Solvent/ Temp. °C. | Yield % |
|---|---|---|---|---|---|---|---|
| 7 | Ind Co COD | CoCl$_2$ 100/30 mins. | Mg act. with C$_1$ - 104 245 | indene 250 | COD 257 | THF/30 | 6.0 |
| 8 | Ind Co COD | CoCl$_2$ 100/30 mins. | Mg act. with I$_2$ 100 | indene 250 | COD 250 | THF/65 | 19.2 |
| 9 | Ind Co COD | CoCl$_2$ 100/20 mins. | Mg/anthracene 108/6.2 | indene 250 | COD 250 | THF/65 | 73.8 |
| 10 | Ind Co COD | Co ac$_2$ 100/35 mins. | Mg/anthracene 200/6.2 | indene 250 | COD 250 | THF/65 | 80.5 |
| 11 | Ind Co COD | Co acac$_3$ 100/40 mins. | Mg/anthracene 300/6.2 | indene 250 | COD 250 | THF/65 | 85.1 |
| 12 | Ind Co COD | Co acac$_3$ 100/35 mins. | Mg/anthracene 300/6.2 | indene 110 | COD 110 | THF/65 | 51.0 |
| 13 | Ind Co COD | Co acac$_3$ 100/30 mins. | Mg/anthracene 300/6.2 | indene 250 | COD 250 | diglyms/ 70-88 | 70.2 |
| 14 | Cp Co COD | Co acac$_3$ 100/20 mins. | Mg/anthracene 300/6.2 | CpH 111 | COD 250 | THF/66 | 79.1 |
| 15 | Cp Co COD | Co(OEt)$_2$ 100/40 mins. | Mg/anthracene 400/7.5 | CpH 250 | COD 250 | THF/65 | 45.1 |
| 16* | MeCpCoCOD | Co acac$_3$ 100/35 mins. | Mg/anthracene 300/6.2 | MeCpH 110 | COD 250 | THF/67 | 71.1 |
| 17* | t-butCpCoCOD | Co acac$_3$ 50/15 mins. | Mg/anthracene 150/3.1 | t-butCpH 57 | COD 125 | THF/65 | 41.7 |
| 18++ | Sime$_3$CpCoCOD | Co acac$_3$ 100/20 mins. | Mg/anthracene 300/6.2 | Me$_3$SiCpH 110 | COD 250 | THF/65 | 70.0 |
| 19* | phenylCpCoCOD | Co acac$_3$ 100/16 mins. | Mg/anthracene 300/6.2 | phenylCpH 90 | COD 250 | THF/69 | approx. 40 |
| 20* | Sime$_3$IndCoCOD | Co acac$_3$ 100/20 mins. | Mg/anthracene 300/6.2 | Sime$_3$-indene 115 | COD 250 | THF/69 | 50.6 |
| 21* | Ind Co NBD | Co acac$_3$ 100/40 mins. | Mg/anthracene 300/6.2 | indene 250 | NBD 250 | THF/69 | 30.5 |

18++ The use of trimethylsilyl cyclopentadienyl cobalt cycloocta-(1,5)-diene as catalyst in the reaction of acetonitrile with acetylene:

0.0458 g (0.1507 mMole) of trimethylsilyl cyclopentadienyl cobalt cycloocta-(1,5)-diene is dissolved in 114.2 g (2.785 moles) of acetonitrile and the resulting solution introduced under suction at room temperature into a 500 ml fine steel autoclave fitted internally with a coil condenser. The acetonitrile is saturated with acetylene at 18 bars, approx. 57.5 g (2.212 moles) of acetylene being added. The contents of the autoclave are then heated to 150° C. over a period of 72 minutes during which the pressure rises to 46 bars. Increasing the reaction temperature to 212° C. over a period of 160 minutes allows the pressure to rise to a maximum of 52 bars. After a total reaction time of 312 minutes, the contents of the autoclave are internally cooled with water to 20° C. over a period of 45 minutes.

g) of toluene and the resulting solution introduced under suction at room temperature into a 500 ml fine steel autoclave equipped with an internal coil condenser. The solution is saturated with acetylene at 16 bars, approximately 21 g (0.808 mole) of acetylene being added. The contents of the autoclave are then heated to 150° C. over a period of 45 minutes, during which the pressure in the autoclave rises to a maximum of 42 bars. The reaction temperature is increased to 202° C. over a period of 120 mins. After a total reaction time of 165 minutes, the contents of the autoclave are internally cooled with water to 20° C. over a period of 40 minutes.

144.5 g of crude product are discharged from the autoclave and the volatile constituents are removed by condensation at $10^{-3}$ Torr, 1.0 g of residue remaining behind. According to analysis by gas chromatography, the condensate (143.3 g) contains 87.8 g of toluene, 41.0 g (0.394 mole) of 2-cyanopyridine, 11.46 g (0.073 mole)

of 2,2'-bipyridyl and 2.44 g (0.031 mole) of benzene, corresponding to an 11.5% 2,2'-bipyridyl solution in toluene. The molar ratio of 2,2'-bipyridyl to benzene amounts to 2.4:1 and the yield of 2,2'-bipyridyl, based on the 2-cyanopyridine reacted, to 66.4%. Conversion: 21.8% of 2,2'-bipyridyl. Catalyst utilization: 613 moles of 2,2'-bipyridyl/g-atom of cobalt or 1632.2 kg of 2,2'-bipyridyl/kg of cobalt.

*Characterization of the new compounds in Table 1:

No. 16: Methyl-$\eta^5$-cyclopentadienyl cobalt cyclooc-ta-(1,5)-diene; yellow-brown crystals melting at $-15°$ C. from pentane by concentration and crystallization at $-80°$ C.

| $^1$H—NMR | (CDCl$_3$, 80 Mhz) |
|---|---|
| $\delta$ H$_1$ | 4.58 (m) |
| $\delta$ H$_2$ | 4.27 (m) |
| $\delta$ H$_3$ | 3.22 (m) |
| $\delta$ H$_4$ | 2.34 (m) |
| $\delta$ H$_5$ | 1.57 (m) |
| $\delta$ H$_6$ | 1.55 (s) |

Mass spectrum: m/e: 246 (M+, 78%); 216 (90%); 138 (100%); 59 (53%).

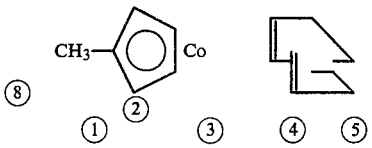

Use as a catalyst:

0.0364 g (0.1480 mMoles) of methyl cyclopentadienyl cobalt cycloocta-(1,5)-diene are dissolved in 119.0 g (2.902 moles) of acetonitrile and the resulting solution introduced under suction at room temperature into a 500 ml fine steel autoclave fitted with an internal coil condenser. The acetonitrile is saturated with acetylene at 15 bars, approximately 50.0 g (1.923 moles) of acetylene being added. The contents of the autoclave are heated to 140° C. over a period of 30 minutes, during which the pressure rises to 48 bars. Increasing the reaction temperature to 180° C. over a period of 72 minutes allows the pressure to rise to its maximum level of 48 bars. After a total reaction time of 120 minutes, the contents of the autoclave are internally cooled with water to 22° C. over a period of 35 minutes.

129.7 g of crude product are discharged from the autoclave and the volatile constituents are removed by condensation at 10$^{-3}$ Torr, 0.1 g of residue remaining behind. According to analysis by gas chromatography, the condensate (128.2 g) contains 99.41 g (2.425 moles) of acetonitrile, 24.16 g (0.260 mole) of 2-picoline and 3.74 g (0.048 mole) of benzene, corresponding to a 19.6% 2-picoline solution in acetonitrile. The molar ratio of 2-picoline to benzene is 5.4:1 and the yield of 2-picoline, based on the acetonitrile reacted, amounts to 54.3%. Conversion: 16.5% of acetonitrile. Catalyst utilization: 1757 moles of 2-picoline/g-atom of cobalt or 2766.8 kg of 2-picoline/kg of cobalt.

No. 17* Tert-butyl-$\eta^5$-cyclopentadienyl cobalt cycloocta(1,5)-diene; dark brown crystals melting at 45° C. After preliminary purification by sublimation at a bath temperature of 80° to 150° C./10$^{-3}$ Torr, the product is obtained from pentane at $-80°$ C.; highly sensitive to air in solution.

Elemental Analysis: Observed: C: 70.93%; H: 8.62%; Co: 20.52%; Calculated: C: 70.82%; H: 8.74%; Co: 20.44%.

| $^1$H—NMR | (d$_8$-toluene, 80 Mhz) |
|---|---|
| $\delta$H$_1$ | 4.60 (t; J = 2.2 Hz) |
| $\delta$H$_2$ | 3.39 (t; J = 2.2 Hz) |
| $\delta$H$_3$ | 3.41 (m) |
| $\delta$H$_4$ | 2.43 (m) |
| $\delta$H$_5$ | 1.65 (m) |
| $\delta$H$_6$ | 1.39 (s) |

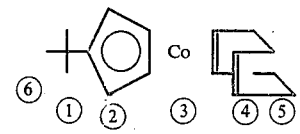

Mass spectrum: m/e: 288 (M+, 61%); 231 (93%); 229 (100%); 164 (54%); 137 (28%); 125 (31%); 59 (47%).

Use as a catalyst:

0.0381 g (0.1321 mMole) of t-butyl cyclopentadienyl cobalt cycloocta-(1,5)-diene are dissolved in 116.25 g (2.835 moles) of acetonitrile and the resulting solution introduced at room temperature into a 500 ml fine steel autoclave fitted with an internal coil condenser. The acetonitrile is saturated with acetylene at 15 bar, approximately 54.0 g (2.077 moles) of acetylene being introduced. The contents of the autoclave are heated to 150° C. over a period of 54 minutes during which the pressure rises to 49 bars. Increasing the reaction temperature to 201° C. over a period of 120 minutes allows the pressure to rise to a maximum level of 54.5 bars. After a total reaction time of 120 minutes, the contents of the autoclave are internally cooled with water to 25° C. over a period of 45 minutes. 132.5 g of crude product are discharged from the autoclave and the volatile constituents are removed by condensation at 10$^{-1}$ Torr, 0.4 g of residue remaining behind. According to analysis by gas chromatography, the condensate (132.0 g) contains 98.93 g (2.413 moles) of acetonitrile, 24.97 g (0.258 moles) of 2-picoline and 4.55 g (0.0583 mole) of benzene, corresponding to a 20.2% 2-picoline solution in acetonitrile. The molar ratio of 2-picoline to benzene is 4.6:1 and the yield of 2-picoline, based on the acetonitrile reacted, amounts to 63.5%. Conversion: 14.9% of acetonitrile. Catalyst utilization: 2032 moles of 2-picoline/g-atom of cobalt or 3203:8 kg of 2-picoline/kg of cobalt.

No. 19: Phenyl-$\eta^5$-cyclopentadienyl cobalt cycloocta-(1,5)-diene; analyzed by chromatography using a 70 cm long SiO$_2$ column (eluent:pentane) and obtained in the form of copper-red flakes melting at 64.3° C. by crystallization from the eluent at $-50°$ C.

Mass spectrum: m/e: 308 (M+, 98%); 278 (68%); 200 (100%); 141 (64%) 59 (42%).

Use as a catalyst:

0.0403 g (0.1308 mMole) of phenyl cyclopentadienyl cobalt cycloocta-(1,5)-diene is dissolved in 116.3 g (2.115 moles) of propionitrile and the resulting solution introduced under suction at room temperature into a 500 ml capacity fine steel autoclave fitted with an internal coil condenser. The propionitrile is saturated with acetylene at 14 bars, approximately 40.5 g (1.558 moles) of acetylene being introduced. The contents of the autoclave are heated to 130° C. over a period of 72 minutes, the pressure rising to 42 bars. Despite an increase in the reaction temperature to 154° C. over a period of 59 minutes, the pressure falls to 39 bars. After a total reaction time of 120 minutes, the contents of the autoclave are internally cooled with water to 20° C. over a period of 30 minutes. 128.5 g of crude product are discharged from the autoclave and the volatile constituents removed by condensation at $10^{-3}$ Torr, 0.1 g of residue remaining behind. According to analysis by gas chromatography, the condensate (128.3 g) contains 103.9 g (0.226 mole) of propionitrile, 20.01 g (0.187 mole) of 2-ethylpyridine and 2.60 g (0.033 mole) of benzene, corresponding to a 16.1% 2-ethylpyridine solution in propionitrile. The molar ratio of 2-ethylpyridine benzene amounts to 5.6:1 and the yield of 2-ethylpyridine, based on the propionitrile reacted, to 82.7%. Conversion: 10.7% of propionitrile. Catalyst utilization: 1430 moles of 2-ethylpyridine/g-atom of cobalt or 2592.9 kg of 2-ethylpyridine/kg of cobalt.

No. 20: Trimethylsilyl-$\eta^5$-indenyl cobalt cycloocta-(1,5)-diene; a deep red oil is obtained by evaporation from pentane and may be distilled at a path temperature of 130°–190° C./$10^{-3}$ Torr, leaving a deep red, highly viscous oil.

Elemental analysis: Observed: C: 67.84%; H: 7.66%; Co: 16.55%; Si: 7.86%; Calculated: C: 67.77%; H: 7.68%; Co: 16.63%; Si: 7.92%.

Mass spectrum: m/e: 354 M+, (100%); 279 (63%); 246 (25%); 59 (17%).

| $^1$H—NMR | (d$_8$-toluene, 80 Mhz) |
|---|---|
| $\delta H_1$ | 5.29 (d, J = 2.7 Hz) |
| $\delta H_2$ | 3.97 (d, J = 2.7 Hz) |
| $\delta H_3$ | 7.50 (m) |
| $\delta H_4$ | 7.08 (m) |
| $\delta H_5$ | 3.50 (m) |
| $\delta H_6$ | 3.03 (m) |
| $\delta H_7$ | 2.08 (m) |
| $\delta H_8$ | 1.35 (m) |
| $\delta H_9$ | 0.34 (s) |
| $^{13}$C—NMR | (d$_8$-toluene) |
| $\delta C_{1/2}$ | 68.43 |
| $\delta C_{2/1}$ | 66.09 |
| $\delta C_{3/4}$ | 31.55 |
| $\delta C_{4/3}$ | 31.29 |
| $\delta C_5$ | 78.78 |
| $\delta C_6$ | 94.51 |
| $\delta C_7$ | 78.87 (s) |
| $\delta C_{8/9}$ | 108.81 (s) |
| $\delta C_{9/8}$ | 108.53 (s) |
| $\delta C_{10/13}$ | 125.04 |
| $\delta C_{13/10}$ | 124.72 |
| $\delta C_{11/12}$ | 123.61 |
| $\delta C_{12/11}$ | 123.52 |
| $\delta C_{14}$ | −0.13 |

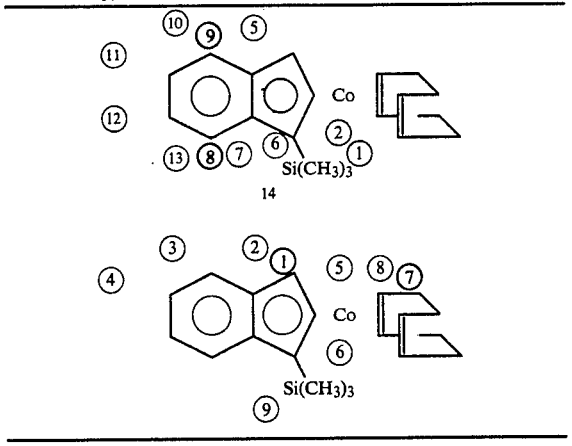

Use as a catalyst:

0.0746 g (0.2108 mMole) of trimethylsilyl indenyl cobalt cycloocta-(1,5)-diene is dissolved in 117.6 g (2.868 moles) of acetonitrile and the resulting solution introduced under suction at room temperature into a 500 ml fine steel autoclave fitted with an internal coil condenser. The acetonitrile is saturated with acetylene at 15 bars, approximately 52.0 g (2.000 moles) of acetylene being introduced. The contents of the autoclave are heated to 90° C. over a period of 20 minutes during which the pressure rises to 34 bars. Increasing the reaction temperature to 170° C. over a period of 82 minutes allows the pressure to rise to a maximum level of 38 bars. After a total reaction time of 142 minutes, the contents of the autoclave are internally cooled with water to 21° C. over a period of 45 minutes.

146.3 g of crude product are discharged from the autoclave and the volatile constituents are removed by condensation at $10^{-3}$ Torr, 0.4 g of residue remaining behind. According to anlaysis by gas chromatography, the condensate (145.6 g) contains 87.31 g (2.130 moles) of acetonitrile, 46.69 g (0.502 mole) of 2-picoline and 7.38 g (0.095 mole) of benzene, corresponding to a 34.8% 2-picoline solution in acetonitrile. The molar ratio of 2-picoline to benzene amounts to 5.3:1 and the yield of 2-picoline, based on the acetonitrile reacted, to 67.9%. Conversion: 27.8% of acetonitrile. Catalyst utilization: 2381 moles of 2-picoline/g-atom of cobalt or 3754.1 kg of 2-picoline/kg of cobalt.

No. 21: $\eta^5$-indenyl cobalt norbornadiene; from pentane by cooling to −80° C. The supernatant mother liquor is removed under pressure from the complex which has crystallized out and the crystals are washed twice with 50 ml of pentane cooled to −80° C. Drying in vacuo ($10^{-1}$ Torr) gives red-brown needles melting at 58° C.

Elemental analysis: Observed: C: 72.32%; H: 5.52%; Co: 22.12%; Calculated: C: 72.19%; H: 5.64%; Co: 22.15%.

| $^1$H—NMR | (d$_8$-toluene, 80 MHz) |
|---|---|
| $\delta H_1$ | 7.14 (s) |
| $\delta H_2$ | 5.75 (t, J = 2.0 Hz) |
| $\delta H_3$ | 4.03 (d, J = 2.0 Hz) |
| $\delta H_4$ | 2.81 (m) |
| $\delta H_5$ | 2.64 (m) |
| $\delta H_6$ | 0.64 (m) |

Mass spectrum: m/e: 266 (M+, 95%); 239 (24%); 174 (50%); 150 (97%); 115 (100%); 59 (40%).

EXAMPLE 22

Regeneration of the anthracene catalyst 11 g (62 mMoles) of anthracene, 3000 ml of THF and 1 ml of methyliodide are added to 72 g (3.00 moles) of magnesium powder (particle size <0.15 mm) in an inert gas atmosphere. A yellow-green solution is formed while stirring at 23° C., orange-colored magnesium anthracene precipitating therefrom after about 2 hours. The reaction mixture is then activated for about 3 hours in an ultrasonic bath, followed by heating with stirring to 65° C. After the addition of 270 g (2.5 moles) of cyclooctadiene and 290 g (2.5 moles) of indene, the heat source is removed and 356 g (1.00 mole) of solid cobalt-(III)-acetylacetonate are introduced over a period of 30 minutes, the reaction mixture changing color to deep red brown with a vigorous heat effect (up to 73° C.).

After cooling to 23° C., the reaction mixture is filtered off from any insoluble fractions and from excess magnesium through a G-3-glass frit and the clear red brown filtrate is concentrated to dryness (max. bath temperature 40° C.) in a high vacuum ($10^{-3}$ Torr). The residue is taken up in 2×3000 ml of hot toluene and the resulting solution is filtered off while still hot from any insoluble residues. The filter cake is washed in portions with a total of 500 ml of hot toluene. Oxygen is passed through the clear, deep red-brown filtrate to oxidize the complex, followed by another hot filtration step. The solution of aromatics is then chromatographed at 60° C. through a 60 cm $Al_2O_3$-column (activity stage 4) and the toluene evaporated in vacuo. Recrystallization from xylene gives 7.6 g of anthracene corresponding to 69% of the catalyst used.

Mass spectrum: m/e: 178 (M+).

EXAMPLE 23

$\eta^3$-methylheptadienyl cobalt butadiene

Following the procedure of Example 1, 2.4 g (100 mMoles) of magnesium powder are activated with 1.1 g (6.2 mMoles) of anthracene in 200 ml of THF and the orange colored reaction mixture cooled to −40° C. After the addition of 200 g (3700 mMoles) of liquid 1,3-butadiene, 13.0 g (100 mMoles) of solid Co-(II) chloride are introduced over a period of 60 minutes, during which the color of the reaction mixture changes via grey-green to grey-brown with a slight increase in temperature (max. −34° C.). After stirring overnight at −40° C., the reaction mixture is cooled to −80° C. and filtered off from any insoluble or precipitated fractions at −80° C. The clear brown filtrate is concentrated in a high vacuum ($10^{-3}$ Torr) at −80° C. to −30° C., the residue is taken up in 150 to 200 ml of ethanol and the complex is crystallized out at −90° C. to −100° C. The supernatant mother liquor is removed under pressure and the crystals are washed twice with 20 ml of pentane cooled to −100° C. Drying in a high vacuum ($10^{-3}$ Torr) at −30° C. gives 13.5 g (60.9 mMoles=60.8%) of methylheptadienyl cobalt butadiene.

Mass spectrum: m/e: 222 (M+).

EXAMPLE 24

Bis-cycloocta-(1,5)-diene nickel-(O)

7.2 g (300 mMoles) of magnesium powder are evacuated together with 1.1 g (6.2 mMoles) of anthracene (Mg:Ant=48:1) and placed in an atmosphere of argon. After suspension in 300 ml of THF dried over $LiAlH_4$, 0.1 ml of ethyl bromide is added. After a few minutes, the solution becomes yellow-green in color and orange-colored magnesium anthracene soon begins to precipitate. The reaction is normally over after 3 hours. The suspension is cooled to 0° C. and 61 ml (54 g-500 mMoles) of cycloocta-(1,5)-diene and approximately 15 ml of liquid butadiene are siphoned in with stirring, followed by the addition of 12.96 g (100 mMoles) of solid anhydrous nickel chloride. The suspension soon becomes dark in color and is left to react overnight while cooling with ice. Hardly any heat effect is observed.

The solution, which has meanwhile become deep violet in color, is freed from excess magnesium by filtration through a D-4-frit and 2 washes with 50 ml of THF (reweighed quantity of Mg approx. 3.5 g), followed by cooling for 3 hours to −80° C. The fine yellow crystals are filtered off at −80° C. by means of a D-4-jacket frit and rinsed twice with a little THF and pentane. They are then completely freed from the deep violet solution and the pale yellow color of the $Ni(COD)_2$ becomes visible. The product is dried for 30 minutes at 23° C. in an oil pump vacuum and subsequently transferred to a suitable vessel. (This intermediate isolation is not absolutely essential). Yield: 21.0 g.

For purification and for complete separation from the $NiCl_2$, the $Ni(COD)_2$ is recrystallized. To this end, it is transferred to a medium-sized D-4-frit, approximately 200 ml of toluene heated to 40° C. are added and, after stirring, the solution is rapidly introduced under pressure into a receiver cooled at ±0° C. The rewashing operation may have to be repeated 1 to 2 times until the crystals are substantially dissolved. The filtrate is cooled for 2 hours at −80° C., the resulting crystals are filtered off through a D-4-frit at −80° C., washed twice with a little pentane, dried and transferred. Yield: 16.5 g of fine lemon-yellow flakes of $Ni(COD)_2$=60% of the theoretical (based on $NiCl_2$).

Elemental analysis: Observed: C: 69.89%; H: 9.06%; Ni 21.12%; Calculated: C: 69.86%; H: 8.79%; Ni 21.34%.

EXAMPLE 25

Bis-cycloocta-(1,5)-diene platinum

Following the procedure of Example 1, 0.49 g (20 mMoles) of Mg are activated with 71 mg (0.4 mMole) of anthracene in 50 of THF, the orange colored reaction mixture is heated to 65° C., 16.2 g (150 mMoles) of 1,5-cyclooctadiene are added and solid platinum-(II)-chloride is introduced over a period of 20 minutes. The reaction mixture becomes red-brown in color with a vigorous heat effect (up to max. 79° C.). After cooling to 23° C., the reaction mixture is concentrated to dryness in a high vacuum ($10^{-3}$ Torr) and the residue is extracted 6 times with 100 ml of toluene. The brown solution is filtered through an $Al_2O_3$-column (5 cm deactivated with 7% of $H_2O$) and the filtrate is concentrated in vacuo to approximately 30 ml. The mother liquor is removed under pressure from the light colored deposit precipitated, followed by washing with cold toluene. Bis-cycloocta-(1,5)-diene platinum is obtained in a yield of 3.7 g (9 mMoles=45%).

Mass spectrum: m/e: 410 (M+); 302.

EXAMPLE 26

Bis-cycloocta-(1,5)-diene palladium

Following the procedure of Example 1, 0.6 g (25 mMoles) of Mg are activated with 90 mg (0.5 mMole) of anthracene in 60 ml of THF and the orange-colored reaction mixture is cooled to −40° C., followed by the addition of 35 ml of cycloocta-(1,5)-diene and 1 ml of 1,3-butadiene. 7.1 g (25 mMoles) of solid cycloocta-(1,5)-diene palladium dichloride are then introduced over a period of 30 minutes. After 1 hour, all the volatile constituents are rapidly distilled off from the dark reaction mixture in a high vacuum ($10^{-3}$ Torr) at −40° C., the residue is taken up in 100 ml of pentane (to which 5 ml of butadiene have been added) and the resulting solution filtered through an $Al_2O_3$-column (5 cm) cooled to −30° C. Concentration of the filtrate gives 1.2 g=15% of the theoretical of product which may be purified by further recrystallization.

EXAMPLE 27

Tris-(butadiene)-molybdenum

Following the procedure of Example 1, 1.5 g (0.84 mMole) of anthracene are added to 3.3 g (135.8 mMoles) of magnesium in 500 ml of THF, followed by activation in an ultrasonic bath. The mixture is then cooled to $-30°$ C. and 23 ml of liquid butadiene are siphoned in. The hydrolysis-sensitive $MoCl_5$ (9.8 g=35.8 mMoles) is introduced into the mixture over a period of 30 minutes in an inert gas atmosphere, initiating a highly exothermic reaction. The reaction mixture turns brown in color even in this short time. The THF is evaporated off at $-10°$ C./$10^{-2}$ Torr and the solid residue is dried at 20° C./$10^{-2}$ Torr. After concentration by evaporation, extraction with toluene gives a tacky crude product which is re-extracted with 100 ml of pentane and recovered by cooling. After dissolution in another 30 ml of THF at 50° C., the solution is cooled to $-20°$ C. The addition of 80 ml of cold ether produces 3.7 g (40% of the theoretical) of $(C_4H_6)_3Mo$.

EXAMPLE 28

Tetrakis-triphenylphosphane palladium

Following the procedure of Example 1, 0.48 g (20 mMoles) of magnesium powder are activated with 0.1 g (0.45 mMole) of anthracene in 40 ml of THF and the orange colored reaction mixture is heated to 65° C., followed by the addition of 21.0 g (80 mMoles) of triphenyl phosphane. 6.1 g (20 mMoles) of solid Pd acac$_2$ are then introduced over a period of 20 minutes. The complex precipitates from the dark orange reaction mixture with evolution of heat (up to 69° C.). After cooling to 23° C., the crystals are filtered off through a G-3-frit and washed with 30 ml of pentane. Drying in vacuo ($10^{-1}$ Torr) gives 20.6 g (17.9 mMoles=89.5% of the theoretical) of yellow crystalline product melting at 116° C.

EXAMPLE 29

Reduction of Pd acac$_2$ with Mg *in the absence of activator*

240 mg (10 mMoles) of magnesium powder are suspended in 40 ml of THF and the resulting suspension treated for 2 hours in an ultrasonic bath, followed by the addition of 10.5 g (40 mMoles) of triphenylphosphane. After heating to 65° C., 3.05 g (10 mMoles) of solid palladium-(II)-acetylacetonate are introduced over a period of 10 minutes, the reaction mixture becoming light brown in color. After stirring for 6 hours at 65° C., a pale yellow compound precipitates. After cooling, the deposit is filtered off and washed with 20 ml of ether, giving 5.9 g of a pale yellow triphenyl phosphine palladium acetylacetonate compound.

Elemental analysis: Observed: Pd: 13.00%; P 9.40%.

Infra-red spectrum: Acetylacetonate bands: 1655; 1550; 1350; 1232 cm$^{-1}$; Triphenylphosphine bands: 1480; 1430; 1180; 1150; 1090; 1020; 995; 510 cm$^{-1}$.

EXAMPLE 30

Bis-(triorthotolylphosphite) nickel ethylene

Following the procedure of Example 1, 2.4 g (100 mMoles) of magnesium powder are activated with 1.1 g (6.2 mMoles) of anthracene in 300 ml of THF and the orange colored reaction mixture is cooled to 0° C. After the addition of 70.5 g (200 mMoles) of triorthotolylphosphite, ethylene gas is introduced through the mixture for 10 minutes and 25.7 g (100 mMoles) of solid nickel-(II)-acetylacetonate are introduced while ethylene gas is continuously passed through. Despite external cooling with ice, the internal temperature rises to 15° C. The reaction mixture is left to react for 3 hours while ethylene is passed through and is then filtered off from any insoluble fractions through a G-3-frit. The yellow-brown filtrate is concentrated to dryness in vacuo ($10^{-1}$ Torr) and the glassy-brittle residue is taken up in 300 ml of pentane and 100 ml of toluene. The solution is filtered off from any insoluble residues and the product is crystallized out by the addition of 100 ml of methanol. Crystallization is completed by cooling to B $-20°$ C. Yield: 51.5 g=65% of the theoretical of yellow crystals melting or decomposing at 118° C.

EXAMPLE 31

Tris-(triorthotolylphosphite) nickel

Following the procedure of Example 1, 1.44 g (60 mMoles) of magnesium powder are activated with 0.66 g (3.7 mMoles) of anthracene in 180 ml of THF. After the addition at 23° C. of 70.5 g (200 mMoles) of triorthotolyphosphite, 15.4 g (60 mMoles) of solid nickel-(II)-acetylacetonate are introduced over a period of 20 minutes. The reaction mixture is freed from volatile constituents in vacuo ($10^{-2}$ Torr) and the residue is taken up in 200 ml of pentane and 70 ml of toluene. The solution is filtered off from any insoluble residues and 150 ml of methanol are added to the filtrate, followed by cooling to $-20°$ C., the complex precipitating in the form of light red crystals. Yield: 50.2 g=75% of the theoretical.

EXAMPLE 32

Pentamethyl-$\eta^5$-cyclopentadienyl cobalt bis-ethylene

Following the procedure of Example 1, 8.3 mg (0.047 mMole) of anthracene in 8 ml of THF are added to 48.2 mg (2.01 mMoles) of fine magnesium powder, followed by additional activation in an ultrasonic bath. Gaseous ethylene is passed through the solution at 0° C. and 893.8 mg (1.99 mMoles) of $[(Co(C_5Me_5)I_2)_2]$ are added all at once. The initially green-black suspension changes into an orange-brown solution which is evaporated at up to 25° C./0.1 Torr. The residue is taken up in 8 ml of pentane, filtered and cooled to $-80°$ C. After a while, orange colored crystals of $Me_5CpCo(C_2H_4)_2$ are obtained in a yield of 373.1 mg, corresponding to 75% of the theoretical.

EXAMPLE 33

Bis-(pentamethyl-$\eta^5$-cyclopentadienyl) zirconium dicarbonyl

Following the procedure of Example 1, 10.1 mg (0.057 mMole) of anthracene in 25 ml in 25 ml of THF are added to 72 mg (2.96 mMoles) of fine magnesium powder, followed by additional activation for 5 hours in an ultrasonic bath. CO is the introduced, steps having to be taken to ensure thorough intermixing. 869.2 mg (2.01 mMoles) of $(\eta^5C_5Me_5)_2Zr\ Cl_2$ are then introduced and the mixture left to react for 2 hours. The dark red solution is concentrated by evaporation to dryness and the residue is taken up in 50 ml of pentane. The solution is filtered off from suspended particles. 696.1 mg (83% of the theoretical) of $(\eta^5C_5Me_5)_2Zr(CO)_2$ in the form of black needles are obtained at $-30°$ C. from the solution concentrated to 20 ml.

EXAMPLE 34

(μ-dichloro) (bis-cyclopentadienyl-titanium)-fulvene

Following the procedure of Example 1, 1.1 g (6.2 mMoles) of anthracene and 42.7 g of cyclopentadiene are added to 10.94 g (450 mMoles) of fine magnesium powder in 300 ml of THF, followed by activation with 0.1 ml of methyliodide and by treatment for 3 hours in an ultrasonic bath. 56.9 g (33 ml=300 mMoles) of TiCl$_4$ are then added dropwise, which initiates an extremely vigorous reaction and an increase in temperature to 69° C. After the addition, the mixture is allowed to cool to 23° C. and 14.8 g of a scarlet-red compound are obtained after 12 hours, being isolated by filtration. Another 69.1 g are obtained from the filtrate by concentration. Total yield: 83.9 g of C$_5$H$_4$—C$_5$H$_4$Ti$_2$(C$_5$H$_5$)$_2$Cl$_2$ corresponding to 179.9 mMoles=66% of the theoretical.

Elemental analysis: Observed: C: 40.05%; H: 5.75%; Ti: 7.26%; Cl: 32.21%.

Mass spectrum: m/e: 424 (M+).

EXAMPLE 35

Cp$_2$TiCl$_2$ 6 g (24.2 mMoles) of pale red Cp$_2$TiCl$_2$ (corresponding to 48.4% of the theoretical) are obtained from a mixture corresponding to Example 34 containing 1.2 g (50 mMoles) of magnesium powder, 0.2 g (1 mMole) of anthracene in 50 ml of THF and also 8.4 g (128 mMoles) of cyclopentadiene and 16.7 g (50 mMoles) of TiCl$_4$.2THF by concentrating the reaction mixture by evaporation to dryness, extraction with CH$_2$Cl$_2$ and crystallization.

Elemental analysis: Observed: C: 45.00%; H: 4.19%; Ti: 18.59%; Cl: 32.5%.

Mass spectrum: m/e: 248 (M+)

EXAMPLE 36

Bis-η$^5$-methylcyclopentadienyl titanium dichloride

Following the procedure of Example 1, 0.18 g (1 mMole) of anthracene is added to 1.2 g (50 mMoles) of magnesium powder in 50 ml of THF, followed by additional activation for 3 hours in an ultrasonic bath. After heating to 65° C., 8 g (100 mMoles) of 1-methylcyclopentadiene are added and 16.7 g (50 mMoles) of solid titanium-(IV)chloride.2THF are introduced over a period of 10 minutes. The reaction mixture changes color via grey-brown to scarlet red with vigorous evolution of heat (up to 70° C.). After cooling to 23° C., the reaction mixture is concentrated to dryness in vacuo (10$^{-2}$ Torr) and the residue is extracted with chloroform, giving 5.92 g (21.46 mMoles=43%) of a yellow-red product.

EXAMPLE 37

η$^5$-(α-methylindenyl)-cobalt cycloocta-(1,5)-diene 1.1 g (6.2 mMoles) of anthracene, 300 ml of THF and 0.1 ml of methyl iodide are added in an inert gas atmosphere to 7.2 g (300 mMoles) of magnesium powder (particle size <0.15 mm). A yellow-green solution is formed while stirring at room temperature, orange colored magnesium anthracene precipitating therefrom after 1 to 2 hours. The reaction mixture is then activated for about 1 hour in an ultrasonic bath and heated while stirring to 65° C. After the addition of 27.32 g (253 mMoles) of CO-1,5-D and 13.84 g (107 mMoles) of α-methyl indene, the heat source, is removed and 35.61 g (100 mMoles) of cobalt-(III)-acetylacetonate are added in portions over a period of 30 minutes, the reaction solution undergoing a change in color to black-red with spontaneous heating to the point of vigorous refluxing (72° C.). After cooling to room temperature, the reaction mixture is stirred overnight (approximately 16 hours), filtered off from unreacted magnesium and insoluble fractions through a G-3-glass frit and the filtrate concentrated to dryness in a high vacuum (10$^{-3}$ mbar). The black-brown residue is taken up in 400 ml of pentane and refiltered through a G-3-glass frit for separation from insoluble fractions. The filter cake is washed in portions with a total of 150 ml of pentane and the red-brown filtrate is concentrated to 100 ml. The complex is then crystallized out by gradual cooling to −80° C. The supernatant mother liquor is removed under pressure, washed twice with 50 ml of pentane cooled to −80° C. and the crystals dried in a high vacuum (10$^{-3}$ mbar). Yield: 14.3 g=48.3 mMoles=48.3% of η$^5$-(α-methylindenyl) cobalt cycloocta-(1,5)-diene, M.p. 72°–73° C.

Elemental analysis: Calculated: C: 72.97%; H: 7.09%; Co: 19.93%; Observed: C: 72.92%; H: 7.14%; Co: 19.98%.

IR-analysis: 2820–3000; 1468; 1452; 1424; 1370; 1335; 1318; 1205; 845; 810 cm$^{-1}$.

| $^1$H—NMR | (d$_8$-toluene) |
|---|---|
| δH$_1$ | 5.59 ppm (d, J = 2.8 Hz) |
| δH$_2$ | 3.82 ppm (d, J = 2.8 Hz) |
| δH$_3$ | 7.20 ppm (m) |
| δH$_4$ | 1.30 ppm (s) |
| δH$_5$ | 3.21 ppm (m) |
| δH$_6$ | 2.12 ppm (m) |
| δH$_7$ | 1.50 ppm (m) |

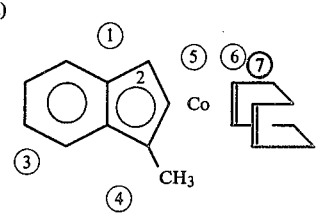

| $^{13}$C—NMR | (d$_8$-toluene) |
|---|---|
| δC$_{1/4}$ | 69.71 ppm |
| δC$_2$ | 31.87 ppm |
| δC$_3$ | 30.81 ppm |
| δC$_{4/1}$ | 67.67 ppm |
| δC$_5$ | 84.97 ppm |

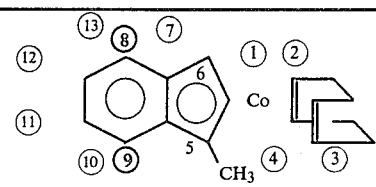

| | | | |
|---|---|---|---|
| $\delta C_6$ | 89.92 ppm | $\delta C_{10/13}$ | 121.06 ppm |
| $\delta C_7$ | 73.86 ppm | $\delta C_{11/12}$ | 124.04 ppm |
| $\delta C_8$ | 105.59 ppm | $\delta C_{13/10}$ | 123.40 ppm |
| $\delta C_9$ | 105.44 ppm | $\delta C_{14}$ | 9.81 ppm |

Mass spectrum: m/e 296 (100%); 266 (44%); 188 (86%); 129 (42%); 128 (60%); 113 (38%); 59 (89%).

EXAMPLE 38

0.36 g (2.0 mMoles) of anthracene and 0.1 ml of ethylbromide are added to 2.43 g (0.10 mole) of magnesium powder (50 mesh) in 150 ml of THF and the resulting suspension is stirred at room temperature until the orange-colored deposit of magnesium anthracene has precipitated (approximately 2 hours). 26 ml (0.3 mole) of liquid butadiene are then added to the suspension at 0° C., followed by the introduction with stirring over a period of 30 minutes of 13.0 g (0.10 mole) of anhydrous $NiCl_2$. After stirring for 20 hours at 0° C., the mixture is cooled to −78° C., filtered off from $MgCl_2$, unreacted magnesium and $NiCl_2$ at that temperature and the filter cake washed with cold THF. The deep red colored filtrate contains 82.5% of the nickel used in soluble form. A 10 ml sample of the filtrate (275 ml in all) takes up 328 ml of $H_2$ during hydrogenation (25° C./1 bar), metallic nickel being quantitatively separated out. The removal of THF and distillation in a high vacuum leaves 0.62 g of saturated hydrocarbons having the following composition (in % by weight, according to analysis by gas chromatography): n-dodecane 76.8, cyclododecane 10.3, n-octane 3.1 and n-hexadecane 0.5% (remainder unknown compounds). The quantity of n-dodecane corresponds to a yield of the $\eta^3,\eta^2,\eta^3$-dodeca-2,6,10-triene-1,13-diyl nickel (I) (Bogdanovic, Heimbach, Kroner, Wilke, Hoffmann and Brandt, Liebigs Ann. Chem. 727, 143 (1969)) of 77% (based on the $NiCl_2$ used). The molar ratio of Ni to n-dodecane amounts to 1.00:0.93 (theoretical 1:1).

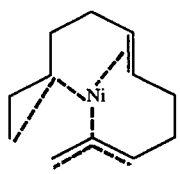

I

For comparison, a test was carried out in the same way using the same quantities of materials, but no anthracene. In this case, only 37% of the nickel used was recovered in solution after filtration at low temperature.

EXAMPLE 39

$\eta^6$-phenylborinato-cobalt cycloocta-(1,5)-diene 24 mg (0.13 mMole) of anthracene, 6 ml of THF and 1 drop of methyliodide are added in an inert gas atmosphere to 146 mg (6 mMoles) of magnesium powder (particle size <0.15 mm). A yellow-green solution is formed while stirring at room temperature, orange-colored magnesium anthracene precipitating therefrom in about 1 to 2 hours. The reaction mixture is activated for about 3 hours in an ultrasonic bath (Sonorex RK 514, a product of the Bandelin company, continuous HF peak output 400 watts, 35 kHz) and then heated while stirring to 60° C. After the addition of 550 mg (5.09 mMoles) of cycloocta-(1,5)-diene and 350 mg (2.27 mMoles) of 1-phenylboracyclohexa-2,5-diene in 4 ml of THF, the heat source is removed and 710 mg (1.99 mMoles) of solid cobalt-(III)-acetylacetonate are introduced over a period of 3 minutes, the reaction mixture changing color to deep orange-brown with spontaneous heating to the point of vigorous refluxing (73° C.). After cooling to room temperature, all the volatile fractions are distilled off in vacuo ($10^{-3}$ mbar), the brittle brown residue is taken up on approximately 80 ml of pentane and the resulting solution filtered off from insoluble residues through a G-3-frit. The complex is crystallized out from the clear orange colored filtrate by gradual cooling to −80° C., the supernatant mother liquor is separated off and the crystals are dried in vacuo ($10^{-1}$ mbar). Yield: 270 mg=0.84 mMole=42.2% of $\eta^6$-phenylborinatocobalt cycloocta-(1,5)-diene, M.p. 169° C. (lit.: 169° C.). Literature: G. E. Herberich, W. Koch and H. Leuken, J. Organomet. Chem. 160 (1978) 17-23.

EXAMPLE 40

$\eta^5$-cyclopentadienyl vanadium 1.1 g (6.2 mMoles) of anthracene, 300 ml of THF and 0.1 ml of methyliodide are added in an inert gas atmosphere to 7.2 g (300 mMoles) of magnesium powder (particle size <0.15 mm). A yellow-green solution is formed with stirring at room temperature, orange colored magnesium anthracene precipitating therefrom in about 1 to 2 hours. The reaction mixture is activated for about 3 hours in an ultrasonic bath (Sonorex RK 514, a product of the Bandelin company, continuous HF peak output 400 watts, 35 kHz) and then heated with stirring to 65° C. After the addition of 26.4 g (400 mMoles) of monomeric cyclopentadiene, 15.7 g (100 mMoles) of solid vanadium-(III)-chloride are introduced over a period of 10 minutes. The reaction mixture is then heated for another 4.5 hours to 60° C. and, after cooling to room temperature, is filtered off from insoluble fractions through a G-3-glass frit. The deep violet filtrate is concentrated to dryness in vacuo ($10^{-1}$ mbar) and the black-violet residue is taken up in approximately 150 ml of pentane. After refiltration through a G-3-glass frit for separation from insoluble fractions, the clear deep violet filtrate is slowly cooled to −80° C. and the complex allowed to crystallize out overnight. The supernatant mother liquor is removed under pressure and the crystals are washed twice with 30 to 40 ml of pentane cooled to −80° C. and dried in vacuo ($10^{-1}$ mbar) at room temperature.

Yield: 3.4 g=18.8 mMoles=18.8% of bis-$\eta^5$-cyclopentadienyl vanadium, M.p. 166° C. (lit.: 167°-168° C.). Literature: E. O. Fischer, W. Hafner, Z. Naturforsch. 96 (1954) 503-504.

EXAMPLE 41

$\eta^5$-cyclopentadienyl cobalt cycloocta-(1,5)-diene (two stages)

1st stage 1.1 g (6.2 mMoles) of anthracene, 150 ml of THF and 0.1 ml of methyliodide are added in an inert gas atmosphere to 7.2 g (300 mMoles) of magnesium powder (particle size <0.15 mm). A yellow-brown solution is formed with stirring at room temperature, orange colored magnesium anthracene precipitating therefrom in approximately 1 to 2 hours. The reaction mixture is cooled to $-25°$ C., followed by the addition of 32.4 g (300 mMoles) of cycloocta-(1,5)-diene. 21.9 g (100 mMoles) of solid cobalt-(II)-bromide are then introduced over a period of 3 hours 20 minutes, the reaction mixture changing color from green to dark grey-green. After stirring overnight at $-30°$ C. (16 hours), 100 ml of toluene cooled to $-30°$ C. are added to the green-black heterogeneous reaction mixture which is filtered off from insoluble residues at $-30°$ C. through a G-3-glass frit with a cooling jacket. The grey-green frit residue is dried for 3 hours in a high vacuum ($10^{-3}$ mbar) and extracted with 400 ml of toluene heated to 80° C., followed by filtration at 80° C. to remove undissolved residues. A green-black solid precipitates from the clear dark green filtrate by gradual cooling to room temperature. After the supernatant mother liquor has been removed under pressure, followed by drying in a high vacuum ($10^{-3}$ mbar), a black-green solid is obtained in a quantity of 2.8 g.

Elemental analysis: Observed: C: 32.56%; H: 4.80%; Co: 7.26%; Mg: 6.83%; Br: 40.37%.

2nd stage 700 mg ( 0.83 mMoles of cobalt) of the green-black solid described above are dissolved in 50 ml of THF and 560 mg (3.15 mMoles) of solid cyclopentadienyl sodium/dimethoxy ethane adduct added to the resulting solution at room temperature. After heating for 6 hours to 60° C., a brown solution and a light deposit are formed. The solution is filtered off from the deposit through a G-4-glass frit and the brown filtrate is concentrated to dryness in a high vacuum ($10^{-3}$ mbar). The residue is taken up in approximately 100 ml of pentane, the resulting solution filtered off from any insoluble residues and the filtrate concentrated to approximately 30 ml. After the addition of 20 ml of oxygen-free water, the mixture is vigorously stirred for about 1 hour. The orange colored organic phase is then isolated and separated up by adsorption chromatography in an approximately 30 cm long Al$_2$O$_3$-column (activity stage II). The orange colored main runnings are concentrated to approximately 10 ml and the complex is crystallized out by cooling to $-80°$ C. The supernatant mother liquor is removed under pressure and the orange colored crystals are dried in vacuo ($10^{-1}$ mbar).

Yield: 19 mg=0.082 mMole=9.9% of $\eta^5$-cyclopentadienyl cobalt cycloocta-(1,5)-diene, M.p. 102° C. (lit.: 103° C.). Literature: R. B. King, P. M. Treichel and F. G. A. Stone, J. Am. Chem. Soc. 83 (1981) 3593–3597.

EXAMPLE 42

$\eta^5$-cyclopentadienyl cobalt cycloocta-(1,5)-diene (two stages)

1st stage 1.1 g (6.2 mMoles) of anthracene, 150 ml of THF and 0.1 ml of methyliodide are added in an inert gas atmosphere to 7.2 g (300 mMoles) of magnesium powder (particle size <0.15 mm). A yellow-green solution is formed while stirring at room temperature, orange colored magnesium anthracene precipitating therefrom in about 1 to 2 hours. The reaction mixture is cooled to $-25°$ C., followed by the addition of 32.4 g (300 mMoles) of cycloocta-(1,5)-diene. 13.0 g (100 mMoles) of cobalt-(II)-chloride are then introduced over a period of 3 hours, the reaction mixture changing color from the blue to grey-green. After stirring for 48 hours at $-30°$ C., 100 ml of toluene cooled to $-30°$ C. are added to the dark grey-green heterogeneous reaction mixture which is then filtered off at $-30°$ C. from any insoluble residues through a G-3-glass frit with a cooling jacket. The grey-green frit residue is washed twice with 200 ml of pentane and dried for 3 hours in a high vacuum ($10^{-3}$ mbar). The grey-green powder is extracted with 500 ml of toluene heated to 80°–90° C., followed by filtration at 80° C. for separation from insoluble residues. A green-black solid is precipitated from the clear dark green filtrate by gradual cooling to room temperature. After the supernatant mother liquor has been removed under pressure, followed by drying in vacuo ($10^{-3}$ mbar), a green black, glistening solid is obtained in a quantity of 19.5 g.

Elemental analysis: Observed: C: 54.76%; H: 8.28%; Co: 7.27%; Mg: 5.71%; Cl: 13.11%.

2nd stage 1.2 g ( 1.5 mMoles of cobalt) of the green-black solid described above are dissolved in 75 ml of THF and 5.2 g (29 mMoles) of solid cyclopentadienyl sodium/dimethoxy ethane adduct are added to the resulting solution at room temperature. After heating overnight to 70° C. (approximately 16 hours), a brown solution and a light voluminous deposit are formed. The solution is filtered off from the deposit through a G-4-glass frit and the brown filtrate is concentrated in a high vacuum ($10^{-3}$ mbar). The oily residue is taken up in 100 ml of pentane, the solution filtered off from any insoluble residues and the clear orange colored filtrate is separated up by adsorption chromatography in an approximately 30 cm long Al$_2$O$_3$-column (activity stage II). The orange-yellow colored main runnings are concentrated to approximately 20 ml and the complexes crystallized out by cooling to $-80°$ C. The supernatant mother liquor is removed under pressure and the orange-brown crystals are dried in vacuo ($10^{-1}$ mbar).

Yield: 27 mg=0.12 mMoles=8% of $\eta^5$-cyclopentadienyl cobalt cycloocta-(1,5)-diene, M.p. 102°–103° C. (lit.: 103° C.). Literature: R. B. King, P. M. Treichel and F. G. A. Stone, J. Am. Chem. Soc. 83 (1981) 3593–3597.

EXAMPLES 43 TO 46

The use of magnesium activated by substituted anthracenes is illustrated by 4 examples for the production of $\eta^5$-indenyl cobalt cycloocta-(1,5)diene.

EXAMPLE 43

The procedure of example 11 is followed except that 6 mMoles 2-methylanthracene is used in place of anthracene.

Yield: 20.3 g (20.3 mMoles=72%).

EXAMPLE 44

The procedure of example 11 is followed except that 6 mMoles 9-methylanthracene is used in place of anthracene.

Yield: 18.3 g (18.3 mMoles=65%).

EXAMPLE 45

The procedure of example 11 is followed except that 6 mMoles 1,4-dimethylanthracene is used in place of anthracene.

Yield: 18.9 g (18.9 mMoles=67%).

EXAMPLE 46

The procedure of example 11 is followed except that 6 mMoles 9,10-diphenylanthracene is used in place of anthracene.

Yield: 16.1 g (16.1 mMoles = 57%).

We claim:

1. $\eta^5$-indenylcobalt-$\eta^5$-cyclopentadienyl.
2. $\eta^5$-methylcyclopentadienyl cobalt cycloocta-(1,5)-diene.
3. $\eta^5$-tert.-butylcyclopentadienyl cobalt cycloocta-(1,5)-diene.
4. $\eta^5$-trimethylsilyl indenyl cobalt cycloocta-(1,5)-diene.
5. $\eta^5$-phenyl cyclopentadienyl cobalt cycloocta-(1,5)-diene.
6. $\eta^5$-indenyl cobalt norbornadiene.

* * * * *